US007595044B2

(12) United States Patent
Wang et al.

(10) Patent No.: US 7,595,044 B2
(45) Date of Patent: *Sep. 29, 2009

(54) ARTERY-AND VEIN-SPECIFIC PROTEINS AND USES THEREFOR

(75) Inventors: Hai U. Wang, Folsom, CA (US); Zhoufeng Chen, St. Louis, MO (US); David J. Anderson, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 72 days.

This patent is subject to a terminal disclaimer.

(21) Appl. No.: 11/028,803

(22) Filed: Jan. 4, 2005

(65) Prior Publication Data

US 2006/0288434 A1 Dec. 21, 2006

Related U.S. Application Data

(63) Continuation of application No. 09/687,652, filed on Oct. 13, 2000, now Pat. No. 6,887,674, which is a continuation-in-part of application No. PCT/US99/08098, filed on Apr. 13, 1999, which is a continuation-in-part of application No. 09/085,820, filed on May 28, 1998, now Pat. No. 6,864,227, which is a continuation-in-part of application No. 09/083,546, filed on May 22, 1998, now abandoned.

(60) Provisional application No. 60/081,757, filed on Apr. 13, 1998.

(51) Int. Cl.
*A61K 39/00* (2006.01)
*C07K 14/00* (2006.01)
*A61K 38/00* (2006.01)

(52) U.S. Cl. ............. 424/130.1; 424/140.1; 424/178.1; 514/2; 530/350

(58) Field of Classification Search ................ None
See application file for complete search history.

(56) References Cited

U.S. PATENT DOCUMENTS

| | | | |
|---|---|---|---|
| 5,512,591 A | 4/1996 | Halperin et al. | |
| 5,624,899 A | 4/1997 | Bennett et al. | |
| 5,635,177 A | 6/1997 | Bennett et al. | |
| 5,693,762 A | 12/1997 | Queen et al. | |
| 5,770,599 A | 6/1998 | Gibson et al. | |
| 5,795,734 A | 8/1998 | Flanagan et al. | |
| 5,824,303 A | 10/1998 | Bartley et al. | |
| 5,864,020 A | 1/1999 | Bennett et al. | |
| 6,015,711 A | 1/2000 | Olson et al. | |
| 6,303,769 B1 | 10/2001 | Cerretti et al. | |
| 6,413,730 B1 | 7/2002 | Holland et al. | |
| 6,440,954 B1 | 8/2002 | Haber et al. | |
| 6,479,459 B1 | 11/2002 | Cerretti et al. | |
| 6,492,140 B2 | 12/2002 | Cerretti et al. | |
| 6,514,497 B1 * | 2/2003 | Briskin et al. | ............ 424/143.1 |
| 6,579,683 B2 | 6/2003 | Wang et al. | |
| 6,864,227 B1 * | 3/2005 | Wang et al. | ................ 514/2 |
| 6,887,674 B1 | 5/2005 | Wang et al. | |
| 6,916,625 B2 | 7/2005 | Wang et al. | |
| 7,163,808 B2 | 1/2007 | Anderson et al. | |
| 2002/0146420 A1 | 10/2002 | Bennett et al. | |
| 2004/0136983 A1 | 7/2004 | Aguet | |
| 2004/0234520 A1 | 11/2004 | Aguet et al. | |

FOREIGN PATENT DOCUMENTS

| | | |
|---|---|---|
| EP | 0633315 A2 | 1/1995 |
| EP | 0999 278 A1 | 5/2000 |
| WO | WO-93/00425 | 1/1993 |
| WO | WO 93/15201 A1 | 8/1993 |
| WO | WO-93/15201 A1 | 8/1993 |
| WO | WO-94/10202 | 5/1994 |
| WO | WO-94/11020 | 5/1994 |
| WO | WO-95/27061 | 10/1995 |
| WO | WO-96/02645 A2 | 2/1996 |
| WO | WO-96/03043 | 2/1996 |
| WO | WO-96/09384 | 3/1996 |
| WO | WO-96/13518 | 5/1996 |
| WO | WO-96/23000 | 8/1996 |
| WO | WO 96/26958 A2 | 9/1996 |
| WO | WO-96/36713 | 11/1996 |
| WO | WO-97/09427 | 3/1997 |
| WO | WO-97/23629 | 7/1997 |
| WO | WO-97/43960 | 11/1997 |
| WO | WO-97/44453 | 11/1997 |
| WO | WO-98/45331 | 10/1998 |
| WO | WO 98/45708 A1 | 10/1998 |
| WO | WO 99/08696 A1 | 2/1999 |
| WO | WO-99/17796 | 4/1999 |
| WO | WO 99/52541 | 10/1999 |
| WO | WO 00/24413 A1 | 5/2000 |
| WO | WO 00/30673 A1 | 6/2000 |
| WO | WO 00/30673 A1 | 6/2000 |

(Continued)

OTHER PUBLICATIONS

Benjamini et al., Immunity, A Short Course, 2nd ed., p. 40 (1992).*

(Continued)

*Primary Examiner*—Marianne P Allen
*Assistant Examiner*—Regina M DeBerry
(74) *Attorney, Agent, or Firm*—Ropes & Gray LLP

(57) ABSTRACT

Arterial and venous endothelial cells are molecularly distinct from the earliest stages of angiogenesis. This distinction is revealed by expression on arterial cells of a transmembrane ligand, called EphrinB2 whose receptor EphB4 is expressed on venous cells. Targeted disruption of the EphrinB2 gene prevents the remodeling of veins from a capillary plexus into properly branched structures. Moreover, it also disrupts the remodeling of arteries, suggesting that reciprocal interactions between pre-specified arterial and venous endothelial cells are necessary for angiogenesis. This distinction can be used to advantage in methods to alter angiogenesis, methods to assess the effect of drugs on artery cells and vein cells, and methods to identify and isolate artery cells and vein cells, for example.

8 Claims, 2 Drawing Sheets

FOREIGN PATENT DOCUMENTS

| WO | WO 02/11785 A2 | 2/2002 |
|---|---|---|
| WO | WO 02/26827 A1 | 4/2002 |
| WO | WO 02/058538 A2 | 8/2002 |
| WO | WO 02/061055 A2 | 8/2002 |
| WO | WO 02/079382 A2 | 10/2002 |
| WO | WO 02/102973 A2 | 12/2002 |
| WO | WO 03/004057 A1 | 1/2003 |
| WO | WO-03/094859 A2 | 11/2003 |
| WO | WO-2004/014292 A2 | 2/2004 |
| WO | WO-2004/091375 A2 | 10/2004 |
| WO | WO-2005/048917 A2 | 6/2005 |
| WO | WO-2005/051307 A2 | 6/2005 |

OTHER PUBLICATIONS

Wang, Jean, "Eph tumour suppression: the dark side of Gleevec," *Nature Cell Biology*, 8:785-786 (2006).

Adams, R.H., et al., "Roles of ephrinB Ligands and EphB Receptors in Cardiovascular Development: Demarcation of Arterial/Venous Domains, Vascular Morphogenesis, and Sprouting Angiogenesis," Genes Dev. 13:295-306 (1999).

Adams, R.H., et al., Eph Receptors and Ephrin Ligands: Essential Mediators of Vascular Development. Trends. Cardiovasc. Med., 10:183-188 (2000).

Andres, A.C. et al., "Expression of two novel eph-related receptor protein tyrosine kinases in mammary gland development and carcinogenesis," Oncogene, vol. 9, pp. 1461-1467, 1994.

Asahara, T. et al., "Isolation of Putative Progenitor Endothelial Cells for Angiogenesis," Science, vol. 275, pp. 964-967, Feb. 14, 1997.

Bennett, B.D. et al., "Molecular cloning of a ligand for the EPH-related receptor protein-tyrosine kinase Htk," Proc. Natl. Acad. Sci. USA, vol. 92, pp. 1866-1870, Mar. 1995.

Bergemann, AD. et al., "ELF-2, a New Member of the Eph Ligand Family, Is Segmentally Expressed in Mouse Embryos in the Region of the Hindbrain and Newly Forming Somites," Molecular and Cellular Biology, vol. 15, No. 9, pp. 4921-4929, Sep. 1995.

Dodelet, V.C. et al., Eph Receptors and Ephrin Ligands: Embryogenesis to Tumorigenesis. Oncogene, 19(49): 5614-19 (2000).

Folkman, J. Antiangiogenic Gene Therapy. Proc. Natl. Acad. Sci. USA. 95:9064-66 (1998).

Folkman, J. Fighting Cancer by Attacking Its Blood Supply. Sci. Am. 275(3): 150-54 (1996).

Folkman, J. et al., "Blood Vessel Formation: What Is Its Molecular Basis?," Cell, vol. 87, pp. 1153-1155, Dec. 27, 1996.

Folkman, J., Angiogenic Therapy of the Human Heart. Circulation. 97(7): 628-29 (1998).

Gale, N. W. et al. Growth Factors Acting Via Endothelial Cell-Specific Receptor Tyrosine Kinases: VEGFs, Angiopoietins, and Ephrins in Vascular Development. Genes Dev. 13:1055-66 (1999).

Gale, N. W., et al. Ephrin-B2 Selectively Marks Arterial Vessels and Neovascularization Sites in the Adult, with Expression in Both Endothelial and Smooth-Muscle Cells. Dev. Biol. 230:151-60 (2001).

Gerety, S.S., et al. Symmetrical Mutant Phenotypes of the Receptor EphB4 and Its Specific Transmembrane Ligand ephrin-B2 in Cardiovascular Development. Mol. Cell. 4:403-14 (1999).

Li, J., et al. Expression of the SM22x Promoter in Transgenic Mice Provides Evidence for Distinct Transcriptional Regulatory Programs in Vascular and Visceral Smooth Muscle Cells. J. Cell Biol. 132:849-59, (1996).

Pandey et al., "Role of B61, the Ligand for the Eck Receptor Tyrosine Kinase, in TNF-a-Induced Angiogenesis", Science, vol. 268, pp. 567-569 (1995).

Pasquale, Current Opinion in Cell Biology, 1997, vol. 9, pp. 608-615.

Pasquale, E.B., "The Eph family of receptors," Curr. Opin. Cell. Biol., 9:608-615 (1997).

Risau, W., Mechanisms of angiogenesis, Nature, vol. 386, pp. 671-674, Apr. 17, 1997.

Shin, D., et al. Expression of EphrinB2 Identifies a Stable Genetic Difference Between Arterial and Venous Vascular Smooth Muscle as Well as Endothelial Cells, and Marks Subsets of Microvessels at Sites of Adult Neovascularization. Dev. Biol. 230:139-150(2001).

Simonet, S., et al., "Venous and Arterial Endothelial Cells Respond Differently to Thrombin and its Endogenous Receptor Agonist," European Journal of Pharmacology 216:135-137 (1992).

Stein, E. et al., "Nck Recruitment to Eph Receptor, EphB1/ELK, Couples Ligan Activation to c-Jun Kinase," J. Biol. Chem., 273(3):1303-1308 (1998).

Stein, E., et al., "Eph Receptors Discriminate Specific Ligan Oligomers to Determine Alternative Signaling Complexes, Attachment, and Assembly Responses," Genes Dev., 12:667-678 (1998).

Sturz, et al., "EphB4 signaling is capable of mediating ephrinB2-induced inhibition of cell migration", Biochemical and Biophysical Research Communications, vol. 313, pp. 80-88 (2004).

The Eph Nomenclature Committee, Cell, 1997, vol. 90, pp. 403-404.

Wang, H. "Transmembrane Ephrin Ligands in Neural and Vascular Development," DAI, 59(11):5721 (1999).

Wang, H.U. et al., "Eph Family Transmembrane Ligands Can Mediate Repulsive Guidance of Trunk Neural Crest Migration and Motor Axon Outgrowth," Neuron, vol. 18, pp. 383-396, Mar. 1997.

Wang, H.U. et al., "Molecular Distinction and Angiogenic Interaction between Embryonic Arteries and Veins Revealed by ephrin-B2 and Its Receptor Eph-B4," Cell, vol. 93, pp. 741-753, May 29, 1998.

Yancopoulos, G.D., et al., "Vasculogenesis, Angioenesis, and Growth Factors: Ephrins Enter the Fray at the Border," Cell, 93: 661-664 (1998).

Yuan, et al., "Syndecan-1 up-regulated by ephrinB2/EphB4 plays dual roles in inflammatory angiogenesis", Blood, vol. 104(4), pp. 1025-1033 (2004).

Zhang, X-Q, et al. Stromal Cells Expressing ephrin-B2 Promote the Growth and Sprouting of Ephrin-B2+ Endothelial Cells. Blood. 98:1028-37 (2001).

Stephenson, S.A., et al., "Receptor protein tyrosine kinase EphB4 is up-regulated in colon cancer," BMC Mol. Biol., 2:15 (2001).

Santa Cruz Biotechnology, Inc., "EphB4 (N-19): sc-7285", retrieved from the Internet: URL:http://www.genetimes.com.cn/support/pd_f-ds/7200-7299/sc-7285.pdf (1999).

Inada et al., "Selective Expression of the Receptor Tyrosine Kinase, HTK, on Human Erythroid Progenitor Cells", Blood, 89(8), pp. 2757-2765 (1997).

Fabes et al., "Accumulation of the Inhibitory Receptor EphA4 May Prevent Regeneration of Corticospinal Tract Axons Following Lesion" *Eur. J. Neurosci.*, 23(7):1721-1730 (2006) (Abstract).

Dermer, Gerald B., "Another Anniversary for the War on Cancer," *Bio/Technology*, 12:320 (1994).

Freshney, R. Ian, Culture of Animal Cells: A Manual of Basic Technique, pp. 3-4 (1983).

Gura, Trisha, "Systems for Identifying New Drugs Are Often Faulty," *Science* 278:1041-1042 (1997).

Bruckner et al., "Tyrosine Phosphorylation of Transmembrane Ligands for Eph Receptors", Science, vol. 275, pp. 1640-1643 (1997).

Andres, A. C. et al., "Expression of two novel eph-related receptor protein tyrosine kinases in mammary gland development and carcinogenesis," *Oncogene*, 9:1461-1467 (1994).

Bennett, B. D. et al., "Molecular cloning of a ligand for the EPH-related receptor protein-tyrosine kinase Htk," *Proc. Natl. Acad. Sci. USA*, 92:1866-1870 (1995).

Chang, M.W., et al., "Adenovirus-Mediated Over-Expression of the Cyclin/Cyclin-Dependent Kinase Inhibitor, p21 Inhibits Vascular Smooth Muscle Cell Proliferation and Neointima Formation in the Rat Carotid Artery Model of Balloon Angioplasty," *J. Clin. Invest.*, 96:2260-2268 (1995).

Feldman, L.J., et al., "Perspectives of Arterial Gene Therapy for the Prevention of Restenosis," *Cardiovasc. Res.*, 32:194-207 (1996).

Glassberg et al., "Cultured endothelial cells derived from the human iliac arteries," in Vitro, 18:859-866 (1982).

Goetz et al., "Long-term serial cultivation of arterial and capillary endothelium from adult bovine brain," *In Vitro Cellular and Developmental Biology*, 21:172-180 (1985).

Guzman, R.J., et al., "In Vivo Suppression of Injury-Induced Vascular Smooth Muscle Cell Accumulation Using Adenovirus-Mediated Transfer of the Herpes Simplex Virus Thymidine Kinase Gene," *Proc. Natl. Acad. Sci. USA*, 91:10732-10736 (1994).

Hausner, C., "Organogenesis Vascular Graft Becomes Physiologically-Responsive Living Tissue After Implantation [online]," *Nature Biotechnol.*, (1999).

Henkemeyer, M., el. al., "Nuk Controls Pathfinding of Commissural Axons in the Mammalian Central Nervous System," *Cell*, 86:35-46 (1996).

Indolfi, C., et al., "Inhibition of Cellular ras Prevents Smooth Muscle Cell Proliferation After Vascular Injury In Vivo," *Nature Med.*, 1(6):541-545(1995).

Kenyon, B.M., et al., "A Model of Angiogenesis in the Mouse Cornea," *Invest Ophthalmol. Vis. Sci.*, 37:1625-1632(1996).

Keogh, M-C, et al., "Design of a Muscle Cell-Specific Expression Vector Utilising Human Vascular Smooth Muscle ?—Actin Regulatory elements," *Gene Therapy*, 6:616-628 (1999).

Kitamura et al (Cancer Research, Aug. 15, 1991, 51:4310-4315).

Lin, P., et al., "Antiangiogenic Gene Therapy Targeting the Endothelium-Specific Receptor Tyrosine Kinase Tie2," *Proc. Natl. Acad. Sci., USA*, 95:8829-8834 (1998).

Mellitzer, G., et al., "Eph Receptors and Ephrins Restrict Cell Intermingling and Communication," Nature, 400:77-82 (1999).

Nakanuma, Y. et al., "Succinylated Wheat Germ Agglutinin Lectin Binding in Intrahepatic Vessels: A New Histochemical Tool," *Arch. Pathol. Lab. Med.*, 117:809-811 (1993).

Niklason, L.E., et al., "Functional Arteries Grown In Vitro," *Science*, 284:489-493 (1999).

Orioli, D., et al., "Sek4 and Nuk Receptors Cooperate in Guidance of Commissural Axons and in Palate Formation," *Embo J.*, 15(22):6035-6049.

Peng et al., "Regulation of Ca2+-activated K+ channels in pulmonary vascular smooth muscle cells: role of nitric oxide," *J. Applied Physiol.*, 81:1264-1272 (1996).

Ramchandran et al., Mettaloprotease-mediated cleavage secretion of pulmonary ACE by vascular endothelial and kidney epithelial cells,: *Am. J. Physiology*, 271:H744-751 (1996).

Thurston et al., "Permeability-related changes revealed at endothelial cell borders in inflamed venules by lectin binding," *American Journal of Physiology*, 271:H2547-H2562 (1996).

van de Wiel et al., "Factors that define the susceptibility of endothelial cells to tumor necrosis factor and lipid A," *Immunopharmacology*, 23:49-56 (1992).

Vector Laboratories, "Wheat Germ Agglutinin (WGA)," [online].

Yamamoto et al., "Differences in Cellular Responses to Mitogens in Arterial Smooth Muscle Cells Derived From Patients With Moyamoya Disease," *Stroke*, 29:1188-1193 (1998).

Staton et al., "Current Methods for Assaying Angiogenesis in vitro and in vivo," Int. J. Exp. Path. 85:233-248 (2004).

Chrencik et al., "Three Dimensional Structure of the EPHB2 Receptor in Complex with an Antagonistic Peptide Reveals an Novel Mode of Inhibition," J. Biol. Chem. pp. 1-22 (2007).

Fox et al., "Invasiveness of Breast Carcinoma Cells and Transcript Profile: Eph Receptors and Ephrin Ligands as Molecular Markers of Potential diagnostic and Prognostic Application," Biochemical and Biophysical Research Communications 318:882-892 (2004).

Bennett, B.D., et al., "Cloning and Characterization of *HTK*, a Novel Transmembrane Tyrosine Kinase of the EPH Subfamily," *The Journal of Biological Chemistry*, 269(19): 14211-14218 (1994).

Bos et al., "PD153035, a Tyrosine Kinase Inhibitor, Prevents Epidermal Growth Factor Receptor Activation and Inhibits Growth of Cancer Cells in a Receptor Number-dependent Manner[1]", Clinical Cancer Research, vol. 3, pp. 2099-2106 (1997).

Boyd et al., "Isolation and Characterization of a Novel Receptor-type Protein Tyrosine Kinase (hek) from a Human Pre-B Cell Line*", The Journal of Biological Chemistry, vol. 267(5), pp. 3262-3267 (1992).

Breier et al., "Angiogenesis in Embryos and Ischemic Diseases", Thrombosis and Haemostosis, vol. 78(1), pp. 678-683 (1997).

Durbin et al., "Eph signaling is required for segmentation and differentiation of the somites", Genes & Development, vol. 12, pp. 3096-3109 (1998).

Easty et al., "Abnormal Protein Tyrosine Kinase Gene Expression During Melanoma Progression and Metastasis", Int. Journal of Cancer, vol. 60, pp. 129-136 (1995).

Folkman and Klagsbrun, "Angiogenic Factors", Science, vol. 235, pp. 442-447 (1987).

Folkman, Judah, "Angiogenesis in cancer, vascular, rheumatoid and other disease", Nature Medicine, vol. 1(1), pp. 27-31 (1995).

Hirai et al., "A Novel Putative Tyrosine Kinase Receptor Encoded by the eph Gene", Science, vol. 238, pp. 1717-1720 (1987).

Kiyokawa et al., "Overexpression of ERK, an EPH Family Receptor Protein Tyrosine Kinase, in Various Human Tumors [1]", "Cancer Research, vol. 54, pp. 3645-3650 (1994).

Lackman et al., "Distinct Subdomains of the EphA3 Receptor Mediate Ligand Binding and Receptor Dinnerization*", The Journal of Biological Chemistry, vol. 273(32) pp. 20228-20237 (1998).

Magal et al., "Rapid Communication: B61, a Ligand for the Eck Receptor Protein-Tyrosine Kinase, Exhibits Neuroptrophic Activity in Cultures of Rat Spinal Cord Neurons", Journal of Neuroscience Research, vol. 43, pp. 735-744 (1996).

Maru et al., "Evolution, Expression, and Chromosomal Location of a Novel Receptor Tyrosine Kinase Gene, eph", Molecular and Cellular Biology, vol. 8(9), pp. 3770-3776 (1988).

Maru et al., "Overexpression confers an oncogenic potential upon the eph gene", Oncogene, vol. 5, pp. 445-447 (1990).

Nikolova et al., "Cell-type specific and estrogen dependent expression of the receptor tyrosine kinase EphB4 and its ligand ephrin-B2 during mammary gland morphogenesis", Journal of Cell Science, vol. 111, pp. 2741-2751 (1998).

Pandey et al., "Role of B61, the Ligand for the Eck Receptor Tyrosine Kinase, in TNF-a-Induced Angiogenesis", Science, vol. 268, pp. 567-569 (1995).

Presta et al., "Humanization of an Anti-Vascular Endothelial Growth Factor Monoclonal Antibody of the Therapy of Solid Tumors and Other Disorders", Cancer Research, vol. 57, pp. 4593-4599 (1997).

Sunassee and Vile, "Tumour angiogenesis: Hitting cancer where it hurts", Current Biology, vol. 7(5), pp. 282-285 (1997).

Twardowski and Gradishar, "Clinical trials of antiangiogenic agents", Current Opinion in Oncology, vol. 9, pp. 584-589 (1997).

Wang et al., "Molecular Distinction and Angiogenic Interactions Between Embryonic Arteries and Veins Revealed by EphrinB2 and its Receptor EphB4", Circulation 98 (17 supp): Abstract No. 341 (1998).

Winlaw, David S., "Angiogenesis in the Pathobiology and Treatment of Vascular and Malignant Diseases", Ann Thorac. Surg., vol. 64, pp. 1204-1211 (1997).

Xu et al., "Function of the Eph-related kinase rtk1 in patterning of the zebrafish forebrain", Nature, vol. 382, pp. 319322 (1996).

Zetter, Bruce R., "Angiogenesis and Tumor Metastasis", Annu. Rev. Med., vol. 49, pp, 407-424 (1998).

Zhou, Renping, "The Eph Family Receptors and Ligands", Pharmacol. Ther., vol. 77(3), pp. 151-181 (1998).

* cited by examiner

US 7,595,044 B2

ARTERY-AND VEIN-SPECIFIC PROTEINS AND USES THEREFOR

RELATED APPLICATIONS

This application is a continuation of U.S. application Ser. No. 09/687,652, filed on Oct. 13, 2000 now U.S. Pat. No. 6,887,674, which is a continuation-in-part of PCT Application No. PCT/US99/08098, filed Apr. 13, 1999, which is a continuation-in-part of U.S. application Ser. No. 09/085,820, filed on May 28, 1998, now U.S. Pat. No. 6,864,227 which is a continuation-in-part of U.S. application Ser. No. 09/083, 546, filed on May 22, 1998 (abandoned), which claims the benefit of U.S. Provisional Application No. 60/081,757 filed on Apr. 13, 1998. The teachings of each of these applications are incorporated herein by reference in their entirety.

BACKGROUND OF THE INVENTION

The process of blood vessel formation is fundamental in both development and disease. The circulatory system is the first organ system to emerge during embryogenesis, and is necessary to nourish the developing fetus. Disorders of the circulatory system, such as coronary artery disease, are a major cause of morbidity and mortality in modern society. Thus, repairing, replacing and promoting the growth of blood vessels is a major target of clinical research and of pharmaceutical development. Conversely, the ingrowth of new capillary networks into developing tumors is essential for the progression of cancer. Thus, the development of drugs that inhibit this process of tumor angiogenesis is an equally important therapeutic goal. Little attention has been paid to the problem of how arteries and veins acquire their distinct identities. Indeed, many people have assumed that the anatomical and functional differences between arteries and veins simply reflect physiological influences, such as blood pressure, oxygenation and shear forces. Additional knowledge of how arteries and veins acquire their respective identities would be valuable in both research and clinical settings.

SUMMARY OF THE INVENTION

The present invention relates to a method of distinguishing between arterial cells (including arterial endothelial cells) and venous cells based on the expression of a protein on arterial cells (arterial endothelial cells) and not on venous cells, and to a wide variety of processes, methods and compositions of matter, including those useful in research and clinical settings, which are based on the difference in expression between the two cells types. As described herein, it has been shown that there is a molecular distinction between arterial endothelial cells (arteries) and venous endothelial cells (veins) and that arterial endothelial cells and venous endothelial cells bear molecular markers which can be used to identify, separate, target, manipulate or otherwise process each cell type specifically (separate from the other). As a result, arteries and veins can now be distinguished from one another, and cell types that make up arteries and veins can be assessed for other genetic molecular or functional differences and targeted, manipulated or otherwise processed individually or separately for research, diagnostic and therapeutic purposes.

The present invention relates to methods of distinguishing and separating arterial cells from vein cells, and more specifically, distinguishing and separating arterial endothelial cells from venous endothelial cells based on their respective molecular markers; methods of selectively targeting or delivering drugs or agents to arteries or veins; methods of altering (enhancing or inhibiting, where "inhibiting" includes partially or completely inhibiting) the function of artery-specific or vein-specific molecular markers or interaction between them (and, thus, enhancing or inhibiting the effect such functions or interactions have on arterial endothelial cells or venous endothelial cells); and methods of screening for drugs which act selectively on arterial cells (and more specifically, on arterial endothelial cells) or venous cells (and more specifically, on venous endothelial cells).

The invention also relates to transgenic nonhuman mammals, such as transgenic mice, in which genes encoding an arterial cell molecular marker or a venous cell molecular marker are altered, either physically or functionally, and their use as "indicator mice" to specifically visualize either arteries or veins, to assess the function of the molecular marker which has been altered and to identify drugs which affect (enhance or inhibit) their function. It further relates to antibodies which bind an arterial cell-specific marker or a venous cell-specific marker; viral or other vectors targeted to arteries or veins by virtue of their containing and expressing, respectively, an arterial cell-specific marker or a venous cell-specific marker; cDNAs useful for preparing libraries to be screened for additional artery- or vein-specific genes, and immortalized cell lines derived from isolated arterial endothelial cells, from venous endothelial cells, or from transgenic animals (e.g., mice) of the present invention.

A molecular marker for an arterial cell or a venous cell is any gene product (protein or RNA or combination thereof) expressed by one of these cell types aid not by the other. Such a marker can be arterial endothelial cell-specific (artery-specific) or venous endothelial cell-specific (vein-specific) products or proteins. In specific embodiments, these can be referred to, respectively, as arterial endothelial cell-specific (artery-specific) ligands and venous endothelial cell-specific (vein-specific) receptors. Such molecular markers can be expressed on cell types in addition to arterial or venous endothelial cells, but are not expressed on both arterial and venous endothelial cells. Molecular markers can include, for example, mRNAs, members of ligand-receptor pairs, and any other proteins such as adhesion proteins, transcription factors or antigens which are not expressed on both cell types. In one embodiment, the molecular marker is a membrane receptor which is the receptor for a growth factor which acts on arteries or veins. In another embodiment the molecular marker is a member of an endothelial cell surface ligand-receptor pair which is expressed on arterial or venous endothelial cells, but not on both. For example, as described in detail herein, a member of the Ephrin family of ligands and a member of the Eph family of receptors which is its receptor are molecular markers for arterial endothelial cells and venous endothelial cells, respectively and are useful to distinguish the two cell types. Any Ephrin family ligand which is expressed on arterial endothelial cells, but not on venous endothelial cells and a venous endothelial cell-specific Eph family receptor which binds the arterial endothelial cell-specific ligand can be used to distinguish between arteries and veins.

In one embodiment, the present invention relates to the discovery that arterial endothelial cells express an Ephrin family ligand and venous endothelial cells express an Eph family receptor which is a receptor of the Ephrin family ligand expressed on the arterial endothelial cells; methods of distinguishing or separating arterial cells (arteries) from venous cells (veins); methods of selectively targeting or delivering drugs or agents to arteries or veins; methods of enhancing or inhibiting angiogenesis, including angiogenesis in tumors, such as by altering (increasing, decreasing or prolonging) activity of at least one member of an Ephrin family ligand-cognate Eph family receptor pair and drugs useful in the methods; and methods of screening for drugs which selectively act on arteries or veins.

It further relates to transgenic nonhuman mammals, such as transgenic mice, which have altered genes encoding an Ephrin family ligand or altered genes encoding an Eph family receptor, such as EphrinB2 knockout mice which contain a tau-lacZ (tlacZ) insertion that marks arteries but not veins or EphB4 knockout mice which contain a reporter construct (e.g., lacZ or alkaline phosphatase gene) in the EphB4 locus; methods of using these mice as "indicator mice" to define and visualize angiogenic processes (e.g., tumor angiogenesis and ischemia-associated cardiac neovascularization) or to screen drugs for their angiogenic or anti-angiogenic effects on arteries or veins in vivo; and cells, such as immortalized cells, derived from the transgenic mice. The present invention also relates to antibodies which bind an artery-specific Ephrin family receptor (e.g., antibodies which bind EprhinB2); antibodies which bind a venous-specific Eph family receptor (e.g., antibodies which bind EphB4); viral or other vectors which are targeted to arteries or veins for vessel-specific gene therapy by virtue of their containing and expressing DNA encoding, respectively, an Ephrin family ligand (e.g., EphrinB2) or an Eph family receptor (e.g., EphB4); cDNAs useful for preparing libraries to be screened for additional artery-specific or vein-specific genes (whose gene products, in turn, might be artery- or vein-specific drug targets) and methods of repairing or replacing damaged arteries or veins by transplantation of isolated arterial or venous endothelial cells, immortalized cell lines derived from them, or synthetic vessels configured from these cells.

As described herein and as is known to those of skill in the art, Ephrin family ligands are divided into two subclasses (EphrinA and EphrinB) and Eph family receptors are divided into two groups (EphA and EphB). As is also known, within each subclass or group, individual members are designated by an arabic number. The invention is described herein with specific reference to EphrinB2 and EphB4, However, other Ephrin family ligand-Eph family receptor pairs which show similar artery- and vein-specific expression and their uses are also the subject of this invention. Similar artery- and vein-specific pairs can be identified by methods known to those of skill in the art.

DETAILED DESCRIPTION OF THE INVENTION

Figure 1:
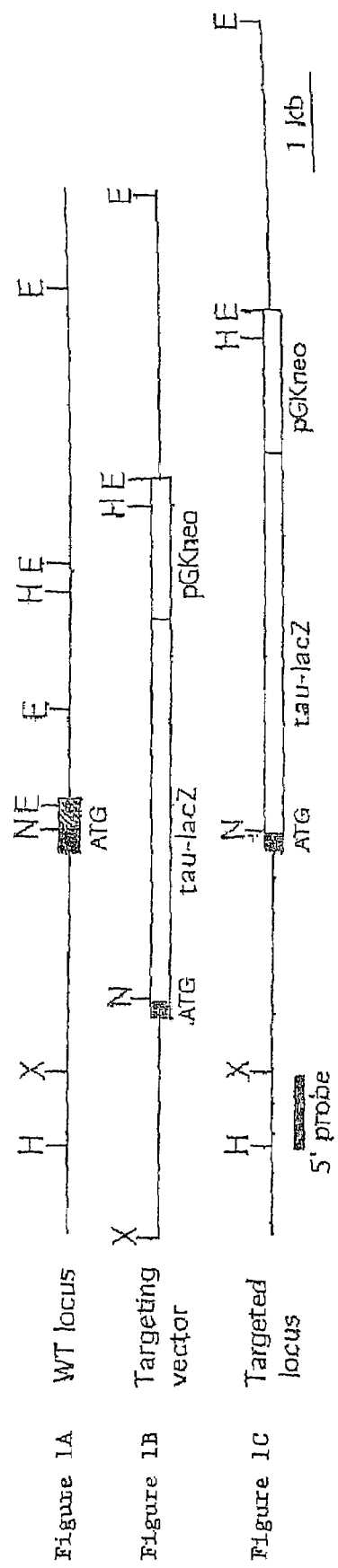
FIG. 1A is a diagram of the wild type locus of the EphrinB2 gene showing the Exon-1 structure. The filled box represents 5' untranslated region. The hatched box starts at the ATG, and includes the signal sequence. H=HindIII; X=XbaI; N=NcoI; E=EcoRI.
FIG. 1B is a diagram of the targeting vector used to disrupt the EphrinB2 gene.
FIG. 1C is a schematic representation of the mutated EphrinB2 locus.

As described herein, it has been shown that arteries and veins are genetically distinct from the earliest stages of embryonic development and that reciprocal interactions between arteries and veins are essential for proper vessel formation. This finding not only changes dramatically our view of the basic ontogenetic anatomy of embryonic vasculature, but also provides the means to distinguish between arterial endothelial cells and venous endothelial cells, both physically and functionally. As a result, means of separating the two cell types from one another; of identifying other artery- or vein-specific genes; of assessing the selective effects of drugs or other agents on arteries or veins and, thus, identifying those which are artery- or vein-specific; and of selectively delivering or targeting substances to either cell type, are now available. In addition, the work described herein makes it possible to modulate (enhance or inhibit) or control vasculogenesis and angiogenesis and to do so, if desired, in an artery-specific or vein-specific manner.

As described in the examples, a gene which encodes a cell membrane-associated ligand which is present in the nervous system and the vascular system has been shown, in adult mice, to be expressed by arterial endothelial cells, and not by venous endothelial cells. Further, the gene which encodes the receptor for the ligands has been shown to be expressed by venous endothelial cells, but not by artery cells. Thus, for the first time, a marker found on arterial endothelial cells (an artery-specific marker) and a venous endothelial cell-(vein-specific) marker are available, making it possible to distinguish between arteries and veins for a variety of purposes, such as further study and understanding of the mechanisms of blood vessel formation; selective targeting of treatments or therapies to arteries or veins (targeting to arteries but not veins or vice versa) and selective modulation (enhancement or inhibition) of formation, growth and survival of arteries and/or veins.

In addition, the work presented in the examples demonstrates that reciprocal signaling between arteries and veins is crucial for vessel morphogenesis (development/formation of arteries and veins). As described, deletion of the ligand-encoding gene in mice prevented the proper development of both arterial and venous vessels. Since the ligand is present on arteries (but not veins), the occurrence of the venous defect is evidence that veins require a signal from arteries for vessel morphogenesis. Conversely, since the arteries are also defective in the mutant mice, the ligand must have a function in the arterial cells themselves, in addition to its role in signaling to the veins. In view of the fact the ligand present on arterial endothelial cells is a transmembrane structure, it most likely functions to receive and transduce to arterial cells a reciprocal signal from venous cells.

Specifically, a ligand which is a member of the Ephrin family of Eph family receptor interactive proteins (Eph family of transmembrane ligands) has been shown to be expressed by arterial endothelial cells, but not by venous endothelial cells. Thus, it is now possible to distinguish between or target arteries and veins by relying on the presence or absence of an Ephrin family ligand and its receptor, which is a member of the Eph family of receptor protein-tyrosine kinases. As described herein, arterial endothelial cells have been shown to express EphrinB2 and venous endothelial cells have been shown to express EphB4, which is an EphrinB2 receptor. EphrinB2 is not expressed on venous endothelial cells and EphB4 is not expressed on arterial endothelial cells, providing a means by which the two cell types can be identified or distinguished and, thus, a means by which arterial endothelial cells and venous arterial cells can be, for example, separated from one another, targeted specifically or acted upon in a selective manner (e.g., by a drug or agent which acts upon one cell type to the exclusion of the other). For example, antibodies that bind to EphrinB2 or to its extracellular domain can be fluorescently labeled and allowed to bind to a mixture of cells, which are then subjected to fluorescent activated cell sorting to select cells of arteries from the mixture.

The work described herein, particularly in the examples, refers to EphrinB2 and EphB4. However, any ligand-receptor pair from the Ephrin/Eph family, any other ligand-receptor pair or any gene product produced by one cell type and not the other (e.g., an Ephrin ligand is expressed by arterial endothelial cells but not by venous endothelial cells and an Eph receptor is expressed by venous endothelial cells but not by arterial endothelial cells) can be used to distinguish between or identify and, thus, selectively act upon, arterial endothelial cells and venous arterial cells.

The ephrins (ligands) are of two structural types, which can be further subdivided on the basis of sequence relationships and, functionally, on the basis of the preferential binding they exhibit for two corresponding receptor subgroups. Structurally, there are two types of ephrins: those which are membrane-anchored by a glycerophosphatidylinositol (GPI) linkage and those anchored through a transmembrane domain. Conventionally, the ligands are divided into the Ephrin-A subclass, which are GPI-linked proteins which bind preferentially to EphA receptors, and the ephrinB subclass, which are transmembrane proteins which generally bind preferentially to EphB receptors.

The Eph family receptors are a family of receptor protein-tyrosine kinases which are related to Eph, a receptor named for its expression in an erythropoietin-producing human hepatocellular carcinoma cell line. They are divided into two subgroups on the basis of the relatedness of their extracellular domain sequences and their ability to bind preferentially to ephrinA proteins or ephrinB proteins. Receptors which interact preferentially with ephrinA proteins are EphA receptors and those which interact preferentially with ephrinB proteins are EphB receptors.

As used herein, the terms Ephrin and Eph are used to refer, respectively, to ligands and receptors. They can be from any of a variety of animals (e.g., mammals/nonmammals, vertebrates/nonvertebrates, including humans). The nomenclature in this area has changed rapidly and the terminology used herein is that proposed as a result of work by the Eph Nomenclature Committee. For convenience, eph receptors and their respective ligand(s) are given in the Table.

| EPH RECEPTORS AND LIGAND SPECIFICITIES | |
|---|---|
| Eph Receptors | Ephrins |
| EphA1 | Ephrin-A1 |
| EphA2 | Ephrin-A3, -A1, A5, -A4 |
| EphA3 | Ephrin-A5, -A2, A3, -A1 |
| EphA4 | Ephrin-A5, -A1, A3, -A2, -B2, -B3 |
| EphA5 | Ephrin-A5, -A1, A2, -A3, -A4 |
| EphA6 | Ephrin-A2, -A1, A3, -A4, -A5 |
| EphA7 | Ephrin-A2, -A3, A1 |
| EphA8 | Ephrin-A5, -A3, A2 |
| EphB1 | Ephrin-B2, -B1, A3 |
| EphB2 | Ephrin-B1, -B2, B3 |
| EphB3 | Ephrin-B1, -B2, B3 |
| EphB4 | Ephrin-B2, -B1 |
| EphB5 | Unknown |
| EphB6 | Unknown |

Ligand specificities are arranged in order of decreasing affinity. Adapted from Pasquale, E. B. (1997) Curr. Opin. Cell Biol. 9(5)608.

The work described herein has numerous research and clinical applications, which are discussed below.

As used herein, a transgenic mouse is one which has, incorporated into the genome of some or all its nucleated cells, a genetic alteration which has been introduced into the mouse or at least one of its ancestors, by the manipulations of man. A transgenic mouse can result, for example, from the introduction of DNA into a fertilized mouse ovum or from the introduction of DNA into embryonic stem cells.

One embodiment of the present invention is a transgenic mouse, which because of its particular genotype, expresses only in cells of veins or only in cells of arteries a gene whose RNA transcript or polypeptide gene product can be detected, for example, by in situ hybridization of RNA, by fluorescence, by detection of enzymatic activity, or by detection of a gene product by antibody binding and a detection system for the bound antibodies.

A particular embodiment of the present invention is a transgenic mouse of genotype EphrinB2$^{+/-}$, wherein the "minus" allele denotes an allele in which a naturally occurring allele has been deleted, modified or replaced with a mutant allele, including a mutant allele which can have an insertion of an indicator gene. Such a "minus" allele can encode an EphrinB2 ligand which has wild type, altered or no ligand function. A mouse of genotype EphrinB2$^{+/tlacZ}$ has been produced as described in Example 1 and used to demonstrate that arterial endothelial cells and venous endothelial cells differ genetically from early stages of development and that reciprocal interactions, essential for proper capillary bed formation, occur between the two types of vessels. A transgenic mouse of the same phenotype can be produced by other methods known to those of skill in the art. Such methods are illustrated below using the EphrinB2 gene as an example, but can also be used for any other vein- or artery-specific gene.

For example, it is possible to produce a vector carrying an insertion, a deletion, or one or more point mutations in the EphrinB2 gene. The EprhinB2 transgene can be introduced into the genome, via a vector carrying a mutagenized EphrinB2 allele, either by introducing the transgene into a fertilized ovum, by the method of Wagner et al., U.S. Pat. No. 4,873,191 (1989), or by introducing the transgene into embryonic stem (ES) cells (see, for example, Capeechi, M. R., Science 244:1288-1292, 1989), or by other methods.

An insertion of DNA used to construct a transgenic knockout mouse can have within it a gene whose presence can be readily tested, such as neo, which confers upon its host cells resistance to G418. It is an advantage of an EphrinB2$^{+/-}$ indicator mouse (e.g., EphrinB2$^{+/taulacZ}$ to be able to express, under the control of the EphrinB2 promoter, an indicator gene, which can be any gene not endogenously expressed by mice. A particularly advantageous indicator gene is one which facilitates the detection of EphrinB2 expression, presumably as it is occurring in the wild type allele, by the production of a gene product that is detectable, for example, by its own light absorbance properties, its ability to act upon a substrate to yield a colored product, or its ability to bind to an indicator or dye which is itself detectable.

Further, alternative methods are available to produce conditional knockouts or tissue specific knockouts of a gene expressed specifically in veins or in arteries (i.e., a vein-specific or artery-specific gene), for example by a site-specific recombinase such as Cre (acting at loxP site) or FLP1 (acting at FRT site) of yeast.

The bacteriophage P1 Cre-loxP recombination system is capable of mediating loxP site-specific recombination in both ES cells and transgenic mice. The site-specific recombinase Cre can also be used in a predefined cell lineage or at a certain stage of development. See, for example, Gu, H. et al., Science 265:103-106, 1994, in which a DNA polymerase β gene segment was deleted from T cells; see also Tsien, J. Z. et al., *Cell* 87:1317-1326, 1996, in which Cre/loxP recombination was restricted to cells in the mouse forebrain.) The impact of the mutation on these cells can then be analyzed.

The Cre recombinase catalyzes recombination between 34 bp loxP recognition sequences (Sauer, B. and Henderson, N., *Proc. Natl. Acad. Sci. USA* 85:5166-5170, 1988). The loxP sequences can be inserted into the genome of embryonic stem cells by homologous recombination such that they flank one or more exons of a gene of interest (making a "floxed" gene). It is crucial that the insertions do not interfere with normal expression of the gene. Mice homozygous for the floxed gene are generated from these embryonic stem cells by conventional techniques and are crossed to a second mouse that arbors a Cre transgene under the control of a tissue type- or cell type-specific transcriptional promoter. In progeny that are homozygous for the floxed gene and that carry the Cre transgene, the floxed gene will be deleted by Cre/loxP recombination, but only in those cell types in which the Cre gene-associated promoter is active.

A gene that encodes a protein which acts to have the effect of mimicking the phenotype caused by mutations in a vein-specific or artery-specific gene can also be used to achieve the same effect as knockouts in vein-specific or artery-specific genes.

A mutation in a gene which encodes a product which prevents binding of ligand to receptor or prevents the functional consequences of such binding and thereby duplicates the phenotype of a vein- or artery-specific gene knockout (e.g., a dominant negative mutant) can be used as an alternative to a knockout. The mutated gene can be put under the control of a tissue-specific promoter to be expressed in vein or artery, depending on the tissue-specific gene product whose function is to be inhibited.

In addition, one or more dominant negative alleles of an artery-specific or vein-specific gene can be put under the control of an inducible promoter so that upon induction, the effect of the inhibition of gene function can be studied. A dominant negative mutant can be isolated or constructed by mutagenesis and methods to make a transgenic mouse.

Testing to identify the desired mutant or wild type alleles, or for the identification of other alleles, can be done by PCR on isolated genomic DNA, using appropriate primers, or by Southern blots using appropriate hybridization probes, by a combination of these procedures, or by other methods.

In addition to the uses of an indicator mouse described in the Examples herein, one use of a mouse having an indicator gene which can mark artery cells is a method for testing an effect of a drug on growth of arteries. The method can comprise administering the drug to a mouse (e.g., embryo, neonate, juvenile, adult, a wound site, tumor, ischemic lesion or arteriovenous malformation in any of the preceding) having an indicator gene inserted in a gene specifically expressed in arteries, and observing the effect of the drug on the growth of the arteries, compared to the effect in a suitable control mouse having an indicator gene, not treated with the drug, but maintained under identical conditions. Similar tests may be performed on an indicator mouse having an indicator gene which marks vein cells. The effect of the drug can be, for example, to promote growth, to inhibit growth, or to promote aberrant growth. Administration of the drug can be by any suitable route known to those of skill in the art.

An indicator mouse having an indicator gene inserted in a gene specifically expressed in artery cells can be crossed with a mouse of another strain carrying a mutation in a gene which is to be tested for its effect on the growth and development of blood vessels, to allow for easier visualization of the effects of the mutation specifically on artery cells. In tests similar to those described above, the effect of a drug can be assessed on the mouse which results from this type of cross, to see, for example, whether the effect of the mutation can be alleviated by the drug. In like manner, an indicator mouse having an indicator gene inserted in a gene specifically expressed in vein cells can be used in a cross with a mouse with a mutation whose effect on growth of veins is to be evaluated, and the resulting hybrid used in studies of the growth of veins.

As a result of the work described herein, it is possible to differentiate between arterial endothelial cells (arteries) and venous endothelial cells (veins) by taking advantage of the presence of an artery-specific or vein-specific gene product on the surface of the cells. Arterial endothelial cells and venous endothelial cells can each be isolated from cells of other tissue types by, for instance, excision of artery or vein tissue from a sample of mammalian tissue, dissociation of the cells, allowing the cells to bind, under appropriate conditions, to a substance which has some property or characteristic (e.g., a molecule which provides a label or tag, or molecule that has affinity for both the an artery-specific cell surface protein and another type of molecule) that facilitates separation of cells bound to the substance from cells not bound to the substance. Separation of the cells can take advantage of the properties of the bound substance. For example, the substance can be an antibody (antiserum, polyclonal or monoclonal) which has been raised against the protein specific to arterial endothelial cells (or to a sufficiently antigenic portion of the protein) and labeled with a fluorochrome, with biotin, or with another label. Separation of cells bound to the substance can be by fluorescence activated cell sorting (FACS), for a fluorescent label, by streptavidin affinity column, for a biotin label, by other affinity-based separation methods, or, for example, by antibody-conjugated magnetic beads or solid supports. "Isolated" as used herein for cells indicates that the cells have been separated from other cell types so as to be a population enriched for a certain cell type, compared to the starting population, and is not limited to the case of a population containing 100% one cell type.

Other means of separation can exploit, for blood vessel cells bearing an indicator insertion in a gene encoding an artery- or vein-specific protein, the properties of the indicator gene product or portion of fusion protein encoded by the indicator insertion. For example, cells producing an artery- or vein-specific fusion protein with a green fluorescent protein portion or a blue fluorescent protein portion can be separated from non-fluorescent cells by a cell sorter. Cells producing a fusion protein having an artery- or vein-specific protein portion and an indicator protein or portion with binding or enzymatic activity can be detected by the ability of the fusion protein to bind to a fluorescent substrate, for example a substrate for β-galactosidase or β-lactamase, or to produce a fluorescent product in cells.

The isolation of arterial endothelial cells and the isolation of venous endothelial cells allows for tests of these cell types in culture to assess the effects of various drugs, growth factors, ligands, cytokines, members of the Eph and Ephrin families of receptors and ligands, molecules that bind to cell surface proteins, or other molecules which can have effects on the growth and development of arteries and veins. One or more of these substances can be added to the culture medium, and the effects of these additions can be assessed (e.g., by measurements of growth rate or viability, enzyme assays, assays for the presence of cell surface components, incorporation of labeled precursors into macromolecules such as DNA, RNA or proteins).

Isolated arterial endothelial cells or isolated venous endothelial cells can be maintained in artificial growth medium, and an immortalized cell line can be produced from each such isolated cell type (i.e., "transformation") by infection with one of any number of viruses (e.g., retroviruses, by transduction of immortalizing oncogenes such as v-myc or SV40 T antigen) known to effectively transform cells in culture. The virus can be chosen for its species specificity of infectivity (e.g., murine ecotropic virus for mouse cells; amphotropic or pseudotyped viruses for human cells). As an alternative to viral transformation, cells can be maintained in culture by propagating the cells in medium containing one or more growth factors.

Immortalized cell lines derived from either vein or artery cells can be used to produce cDNA libraries to facilitate study of genes actively expressed in each of these tissues. Further, such cell lines can be used to isolate and identify proteins expressed in the cells, for instance, by purifying the proteins from conditioned growth medium or from the cells themselves.

As one alternative to using immortalized cell lines of arterial or venous origin, cells or cell lines of non-arterial origin or non-venous origin (e.g., endothelial cells from other tissues, or fibroblasts) can be genetically altered (by the introduction of one or more non-endogenously expressed genes) to express an artery-specific or vein-specific cell surface protein, and used in methods to detect and identify substances that interfere with receptor-ligand interaction.

Introduction of one or more genes into a cell line can be, for instance, by transformation, such as by electroporation, by calcium phosphate, DEAE-dextran, or by liposomes, using a vector which has been constructed to have an insertion of one or more genes. See Ausubel, F. M. et al, *Current Protocols in Molecular Biology*, chapter 9, containing supplements through Supplement 40, Fall, 1997, John Wiley & Sons, New York. The introduction of one or more genes to be expressed in a cell line can also be accomplished by viral infection, for example, by a retrovirus. Retroviral gene transfer has been used successfully to introduce genes into whole cell populations, thereby eliminating problems associated with clonal variation.

The ability to differentiate and to isolate the cells of veins and arteries allows for a wide variety of applications for a wide variety of purposes. For example, it is now possible to assess the effects of various agents, such as drugs, diagnostic reagents and environmental/dietary factors, on arteries and veins and to determine if the effects observed are common to both types of cells or specific to one cell type.

For example, it can no longer be assumed that angiogenic and anti-angiogenic factors or drugs act equivalently on arterial and venous cells. Isolation of these cell types of these tissues, which is made possible by the present work, allows testing of these angiogenic and anti-angiogenic factors for arterial or venous specificity, which will provide more selective clinical indications for these drugs. It will also allow the discovery of new artery- or vein-selective drugs, such as by high-throughput screening of immortalized arterial or venous endothelial cell lines. Existing drugs can also be selectively targeted to arteries or veins by using the proteins described herein as targeting devices (e.g., liposomes or viral vehicles having the protein or an extracellular domain portion thereof on the viral surface) to deliver drugs (e.g., chemically coupled drugs) to one type of vessel or the other. For example, artery-specific agents can be used to promote collateral growth of arteries to bypass coronary artery occlusions or ischemic lesions.

There are numerous approaches to screening agents for their selective effects (angiogenic or anti-angiogenic, affecting vasotension, or inhibiting formation of atherosclerotic plaques) on arteries and veins. For example, high-throughput screening of compounds or molecules can be carried out to identify agents or drugs which act selectively on arteries or veins or, in some cases, on both. Test agents to be assessed for their effects on artery or vein cells can be any chemical (element, molecule, compound), made synthetically, made by recombinant techniques or isolated from a natural source. For example, test agents can be peptides, polypeptides, peptoids, sugars, hormones, or nucleic acid molecules, such as antisense nucleic acid molecules. In addition, test agents can be small molecules or molecules of greater complexity made by combinatorial chemistry, for example, and compiled into libraries. These libraries can comprise, for example, alcohols, alkyl halides, amines, amides, esters, aldehydes, ethers and other classes of organic compounds. Test agents can also be natural or genetically engineered products isolated from lysates or growth media of cells—bacterial, animal or plant—or can be the cell lysates or growth media themselves. Presentation of test compounds to the test system can be in either an isolated form or as mixtures of compounds, especially in initial screening steps.

The compounds or molecules (referred to collectively as agents or drugs) which are screened can be those already known to have angiogenic, anti-angiogenic activity, anti-plaque activity or vasoactivity, or those of unknown effectiveness. In the case of those agents of known effect, the screening will be useful to identify those drugs which act selectively on arterial endothelial cells or on venous endothelial cells. In the case of those agents of unknown effect, screening will be useful to newly identify drugs which have angiogenic, anti-angiogenic activity, anti-plaque activity or vasoactivity, and to establish the cell type (arterial, venous) on which they act. For example, immortalized cell lines of arterial or venous origin can be used to screen libraries of compounds to identify drugs with artery- or vein-specific drug effects.

In one embodiment, an assay can be carried out to screen for drugs that specifically inhibit binding of an Ephrin ligand to its Eph receptor, such as binding of EphrinB2 to the EphB4 receptor, or vice-versa, by inhibition of binding of labeled ligand- or receptor-Fc fusion proteins to immortalized cells. Alternatively, such libraries can be screened to identify members which enhance binding of an Ephrin ligand to its Eph receptor by enhancing binding of labeled ligand- or receptor-Fc fusion proteins to immortalized cells. Drugs identified through this screening can then be tested in animal models (e.g., models of cancer, arteriovenous malformations or coronary artery disease) to assess their activity in vivo.

A drug that inhibits interaction of an artery-specific cell surface molecule (e.g., an arterial endothelial cell-specific surface molecule) with a vein-specific cell surface molecule (e.g., a veinous endothelial cell-specific surface molecule) can be identified by a method in which, for example, the arterial endothelial cell-specific surface molecule and the venous endothelial cell-specific surface molecule are combined with a drug to be assessed for its ability to inhibit interaction between the cell-specific molecules, under conditions appropriate for interaction between the cell-specific molecules. The cell-specific molecules may be used in the assay such that both are found on intact cells in suspension (e.g., isolated arterial or venous endothelial cells, immortalized cells derived from these, or cells which have been modified to express an artery- or vein-specific cells surface molecule); one cell type is fixed to a solid support, and the other molecule specific to the other cell type is in soluble form in a suitable solution; or the molecule specific to one cell type is fixed to a solid support while the molecule specific to the other cell type is found free in a solution that allows for interaction of the cell-specific molecules. Other variations are possible to allow for the convenient assessment of the interaction between the two different cell-specific molecules.

In further steps of the assay, the extent to which the cell-specific molecules interact is determined, in the presence of the drug, and in a separate test (control), in the absence of the drug. The extent to which interaction of the cell-specific molecules occurs in the presence and in the absence of the drug to be assessed is compared. If the extent to which interaction of the cell-specific molecules occurs is less in the presence of the drug than in the absence of the drug, the drug is one which inhibits interaction of the arterial endothelial cell-specific molecule with the venous endothelial cell-specific molecule. If the extent to which interaction of the cell-specific molecules occurs is greater in the presence of the drug than in the absence of the drug, the drug is one which enhances interaction of the arterial endothelial cell-specific molecule with the venous endothelial cell-specific molecule.

In one embodiment of an assay to identify a substance that interferes with interaction of two cell surface molecules, one specific to artery and the other specific to vein (e.g., binding of a ligand to a receptor that recognizes it; interaction between adhesion proteins; interaction between a cell surface protein and a carbohydrate moiety on a cell surface), samples of cells expressing one type of cell surface molecule (e.g., cells expressing an Eph receptor, such as a a vein-derived cell line or other cells genetically manipulated to express the Eph receptor) are contacted with either labeled ligand (e.g., an ephrin ligand, a soluble portion thereof, or a soluble fusion protein such as a fusion of the extracellular domain and the Fc domain of IgG) or labeled ligand plus a test compound or group of test compounds. The amount of labeled ligand which has bound to the cells is determined. A lesser amount of label (where the label can be, for example, a radioactive isotope, a fluorescent or colorimetric label) in the sample contacted with the test compound(s) is an indication that the test compound(s) interferes with binding. The reciprocal assay using cells expressing a ligand (e.g., an Ephrin ligand or a soluble form thereof) can be used to test for a substance that interferes with the binding of a receptor or soluble portion thereof.

An assay to identify a substance which interferes with interaction between artery-specific and vein-specific cell surface protein can be performed with the component (e.g., cells, purified protein, including fusion proteins and portions having binding activity) which is not to be in competition with a test compound, linked to a solid support. The solid support can be any suitable solid phase or matrix, such as a bead, the wall of a plate or other suitable surface (e.g., a well of a microtiter plate), column pore glass (CPG) or a pin that can be submerged into a solution, such as in a well. Linkage of cells or purified protein to the solid support can be either direct or through one or more linker molecules.

Upon the isolation from a mammal of a gene expressing an artery-specific or a vein-specific protein, the gene can be incorporated into an expression system for production of a recombinant protein or fusion protein, followed by isolation and testing of the protein in vitro. The isolated or purified protein can also be used in further structural studies that allow for the design of agents which specifically bind to the protein and can act as agonists or antagonists of the receptor or ligand activity of the protein.

In one embodiment, an isolated or purified artery-specific or vein-specific protein can be immobilized on a suitable affinity matrix by standard techniques, such as chemical cross-linking, or via an antibody raised against the isolated or purified protein, and bound to a solid support. The matrix can be packed in a column or other suitable container and is contacted with one or more compounds (e.g., a mixture) to be tested under conditions suitable for binding of the compound to the protein. For example, a solution containing compounds can be made to flow through the matrix. The matrix can be washed with a suitable wash buffer to remove unbound compounds and non-specifically bound compounds. Compounds which remain bound can be released by a suitable elution buffer. For example, a change in the ionic strength or pH of the elution buffer can lead to a release of compounds. Alternatively, the elution buffer can comprise a release component or components designed to disrupt binding of compounds (e.g., one or more ligands or receptors, as appropriate, or analogs thereof which can disrupt binding or competitively inhibit binding of test compound to the protein).

Fusion proteins comprising all of, or a portion of, an artery-specific or a vein-specific protein linked to a second moiety not occurring in that protein as found in nature can be prepared for use in another embodiment of the method. Suitable fusion proteins for this purpose include those in which the second moiety comprises an affinity ligand (e.g., an enzyme, antigen, epitope). The fusion proteins can be produced by the insertion of a gene specifically expressed in artery or vein cells or a portion thereof into a suitable expression vector, which encodes an affinity ligand. The expression vector can be introduced into a suitable host cell for expression. Host cells are disrupted and the cell material, containing fusion protein, can be bound to a suitable affinity matrix by contacting the cell material with an affinity matrix under conditions sufficient for binding of the affinity ligand portion of the fusion protein to the affinity matrix.

In one aspect of this embodiment, a fusion protein can be immobilized on a suitable affinity matrix under conditions sufficient to bind the affinity ligand portion of the fusion protein to the matrix, and is contacted with one or more compounds (e.g., a mixture) to be tested, under conditions suitable for binding of compounds to the receptor or ligand protein portion of the bound fusion protein. Next, the affinity matrix with bound fusion protein can be washed with a suitable wash buffer to remove unbound compounds and non-specifically bound compounds without significantly disrupting binding of specifically bound compounds. Compounds which remain bound can be released by contacting the affinity matrix having fusion protein bound thereto with a suitable elution buffer (a compound elution buffer). In this aspect, compound elution buffer can be formulated to permit retention of the fusion protein by the affinity matrix, but can be formulated to interfere with binding of the compound(s) tested to the receptor or ligand protein portion of the fusion protein. For example, a change in the ionic strength or pH of the elution buffer can lead to release of compounds, or the elution buffer can comprise a release component or components designed to disrupt binding of compounds to the receptor or ligand protein portion of the fusion protein (e.g., one or more ligands or receptors or analogs thereof which can disrupt binding of compounds to the receptor or ligand protein portion of the fusion protein).

Immobilization can be performed prior to, simultaneous with, or after contacting the fusion protein with compound, as appropriate. Various permutations of the method are possible, depending upon factors such as the compounds tested, the affinity matrix selected, and elution buffer formulation. For example, after the wash step, fusion protein with compound bound thereto can be eluted from the affinity matrix with a suitable elution buffer (a matrix elution buffer). Where the fusion protein comprises a cleavable linker, such as a thrombin cleavage site, cleavage from the affinity ligand can release a portion of the fusion with compound bound thereto. Bound compound can then be released from the fusion protein or its cleavage product by an appropriate method, such as extraction.

One or more compounds can be tested simultaneously according to the method. Where a mixture of compounds is tested, the compounds selected by the foregoing processes can be separated (as appropriate) and identified by suitable methods (e.g., PCR, sequencing, chromatography). Large combinatorial libraries of compounds (e.g., organic compounds, peptides, nucleic acids) produced by combinatorial chemical synthesis or other methods can be tested (see e.g., Ohlmeyer, M. H. J. et al., *Proc. Natl. Acad. Sci. USA* 90:10922-10926 (1993) and DeWitt, S. H. et al., *Proc. Natl. Acad. Sci. USA* 90:6909-6913 (1993), relating to tagged compounds; see also, Rutter, W. J. et al., U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible. Where compounds do not carry tags, chromatographic separation, followed by mass spectrophotometry to ascertain structure, can be used to identify individual compounds selected by the method, for example.

An in vivo assay useful to identify drugs which act selectively on arteries or on veins is also available. It is carried out using transgenic animals, such as those described herein, which make it possible to visualize angiogenic processes. For example, an EphrinB2 knockout mouse containing a marker, such as a tau-lacZ insertion, that marks all arteries but not veins, can be used for a variety of in vivo assays. Other marker genes that can be used, for instance, are genes expressing alkaline phosphatase, blue fluorescent protein or green fluorescent protein. The mouse, or the targeted allele it contains, can be used to study angiogenic processes, such as tumor angiogenesis and ischemia-associated cardiac neovascularization, in arteries, independent of veins. For example, tumor cells can be implanted in the indicator mouse and arterial vessel growth into the tumor can be visualized by lacZ staining. Alternatively, mice bearing the targeted allele can be crossed with a mouse model of another condition, such as vascular degeneration or neovascularization, to be visualized. The arterial-specific aspects of the process can be visually monitored by lacZ staining. An indicator of this type can also be used to assess drugs for their angiogenic or anti-angiogenic effects.

A gene product produced specifically by arterial endothelial cells (arteries) and not by other cell types allows for the specific targeting of drugs, diagnostic agents, tagging labels, histological stains or other substances specifically to arteries. In an analogous manner, a gene product identified as produced specifically by venous endothelial cells (veins) and not detectably produced by other cell types allows for the specific targeting and delivery of drugs, diagnostic agents, tagging labels, histological stains or other substances specifically to veins. The following description of targeting vehicles, targeted agents and methods is presented using EphrinB2 as an illustration of a gene product produced by arterial endothelial cells and not by vein cells and EphB4 as an illustration of a gene product produced by venous endothelial cells and not by artery cells. However, this description applies equally well to other artery-specific and vein-specific gene products that can be used to identify these tissue types.

The differential expression of EphrinB2 in arteries and of Eph4 in veins allows for the specific targeting of drugs, diagnostic agents, imaging agents, or other substances to the cells of arteries or of veins. A targeting vehicle can be used for the delivery of such a substance. Targeting vehicles which bind specifically to EphrinB2 or to Eph4 can be linked to a substance to be delivered to the cells of arteries or veins, respectively. The linkage can be via one or more covalent bonds, or by high affinity non-covalent bonds. A targeting vehicle can be an antibody, for instance, or other compound which binds either to EphrinB2 or to EphB4 with high specificity. Another example is an aqueously soluble polypeptide having the amino acid sequence of the extracellular domain of EphB4, or a sufficient portion of the extracellular domain (or a polypeptide having an amino acid sequence conferring a similar enough conformation to allow specific binding to EphrinB2), which can be used as a targeting vehicle for delivery of substances to EphrinB2 in arteries. Similarly, a soluble polypeptide having the amino acid sequence of the extracellular domain of EphrinB2 or a sufficient antigenic portion of the extracellular domain (or a polypeptide having an amino acid sequence conferring a similar enough conformation to allow specific binding to EphB4), can be used to target substances to EphB4 in veins.

Targeting vehicles specific to an artery-specific Ephrin ligand (e.g., EphrinB2) or to a vein-specific Eph receptor (e.g., EphB4) have in vivo (e.g., therapeutic and diagnostic) applications. For example, an antibody which specifically binds to EphrinB2 can be conjugated to a drug to be targeted to arteries (e.g., a therapeutic, such as an anti-plaque agent). Alternatively, an antibody which specifically binds to EphB4 can be used to target a drug to veins. A substance (e.g., a radioactive substance) which can be detected (e.g., a label) in vivo can also be linked to a targeting vehicle which specifically binds to an artery-specific Ephrin ligand (e.g., EphrinB2) and the conjugate can be used as a labeling agent to identify arteries. Similarly, a detectable label can be linked to a targeting vehicle which specifically binds a vein-specific Eph receptor (e.g., EphB4) to identify veins.

Targeting vehicles specific to EphrinB2 or to EphB4 find further applications in vitro. For example, an EphB4-specific targeting vehicle, such as an antibody (a polyclonal preparation or monoclonal) which specifically binds to EphB4, can be linked to a substance which can be used as a stain for a tissue sample (e.g., horseradish peroxidase) to provide a method for the identification of veins in a sample. Likewise, an antibody which specifically binds to EphrinB2 or to the extracellular domain of EphrinB2 can be used in the identification of arteries. For instance, in a biopsied tissue sample, as from a tumor, or from an arteriovenous malformation in a child or adult, antibody to EphrinB2 or to the extracellular domain of EphrinB2 can be used to identify artery tissue and to distinguish it from vein tissue.

To treat malformed, painful or cosmetically undesirable veins, an agent which acts against them (e.g., antiangiogenic factors) can be linked to an EphB4-specific vehicle for local administration to the veins. For example, anti-angiogenic factors can be injected into varicose veins.

Targeted agents directed to either an artery-specific Ephrin family ligand (e.g., EphrinB2) or a vein-specific Eph family receptor (e.g., EphB4) can also be used when it is desired to produce an effect on both arteries and veins. For example, limited amounts of targeted agents comprising an anti-angiogenic drug and a targeting vehicle to either EphrinB2, EphB4, or both, can be administered locally to sites of angiogenesis, such as sites of tumor formation or sites of undesirable neovascularization where it is desired to inhibit the growth of blood vessels, or to areas in which increased vascularization is desired to enhance growth or establishment of blood vessels.

Substances that act as agonists or antagonists of an artery-specific Ephrin family ligand (e.g., EphrinB2) or a vein-specific Eph family receptor (e.g., EphB4) can be used as angiogenic or anti-angiogenic agents. Drugs that target these molecules will selectively influence arterial and venous angiogenesis. For example, monoclonal antibodies to EphrinB2 or EphB4 can serve as artery- or vein-specific angiogenic or anti-angiogenic agents. Drugs that interfere with EphrinB2 function (for instance, blocking antibodies) can be used in anti-angiogenic methods of therapy. As can be concluded from the phenotype shown by the EphrinB2$^{tlacZ}$/EphrinB2$^{tlacZ}$ mutant mice, antagonists of EphrinB2 or antagonists of EphB4 will inhibit angiogenesis. Agents which are agonists of both EphrinB2 and EphB4 will promote angiogenesis.

In another example, soluble agonists which comprise the extracellular domain of an Ephrin family ligand or the extracellular domain of an Eph family receptor fused to the Fc domain of human IgG can be produced. For example, an EphB4 or an EphrinB2 hybrid protein in which the extracellular domain of the membrane protein is fused to the Fc domain of human IgG can be used (Wang, H. U. and D. J. Anderson, Neuron 18:383-396 (1997)). See, for examples of methods Stein, E. et al., Genes and Dev. 12:667-678 (1998), regarding experiments on responses of cells to clustered Ephrin-B1/Fc fusion proteins. Clustering of these hybrid molecules with anti-human Fc antibodies generates soluble agonists: Ephrin-derived "ligand-bodies" for Eph receptors, and conversely, Eph-derived "receptor bodies" for Ephrins. Nonclustered forms of these hybrid molecules can be used as antagonists.

A further application of isolated arterial endothelial cells and isolated venous endothelial cells is the genetic alteration of the isolated cells and the administration of these cells, preferably intravenously, to the host mammal from which the cells were isolated, or into another compatible host, where the cells can be incorporated into a blood vessel of the appropriate type. In this way, the effects of a genetic defect which is manifested in arteries or in veins can be ameliorated. It has been demonstrated that circulating endothelial cell progenitors can migrate to sites of neovascularization and be incorporated into blood vessels (Asahara et al., Science 275:964-967 (1997)).

The introduction of a gene (an endogenous gene that has been altered, or a gene originally isolated from a different organism, for example) into cells can be accomplished by any of several known techniques, for example, by vector mediated gene transfer, as by amphotropic retroviruses, calcium phosphate, or liposome fusion, for example.

A gene intended to have an effect on arteries or veins in a host mammal can be delivered to isolated artery cells or isolated vein cells by the use of viral vectors comprising one or more nucleic acid sequences encoding the gene of interest. Generally, the nucleic acid sequence has been incorporated into the genome of the viral vector. In vitro, the viral vector containing the nucleic acid sequences encoding the gene can be contacted with a cell and infection can occur. The cell can then be used experimentally to study, for example, the effect of the gene on growth of artery or vein cells in vitro or the cells can be implanted in a patient for therapeutic use. The cells to be altered by introduction or substitution of a gene can be present in a biological sample obtained from the patient and used in the treatment of disease, or can be obtained from cell culture and used to dissect developmental pathways of arteries and veins in in vivo and in vitro systems.

After contact with the viral vector comprising a nucleic acid sequence encoding the gene of interest, the treated artery or vein cells can be returned or readministered to a patient according to methods known to those practiced in the art. Such a treatment procedure is sometimes referred to as ex vivo treatment. Ex vivo gene therapy has been described, for example, in Kasid, et al., Proc. Natl. Acad. Sci. USA 87:473 (1990); Rosenberg, et al., New Engl. J. Med. 323:570 (1990); Williams, et al., Nature 310476 (1984); Dick, et al., Cell 42:71 (1985); Keller, et al., Nature 318:149 (1985) and Anderson, et al., U.S. Pat. No. 5,399,346 (1994).

Generally, viral vectors which can be used therapeutically and experimentally are known in the art. Examples include the vectors described by Srivastava, A., U.S. Pat. No. 5,252,479 (1993); Anderson, W. F., et al., U.S. Pat. No. 5,399,346 (1994); Ausubel et al., "Current Protocols in Molecular Biology", John Wiley & Sons, Inc. (1998). Suitable viral vectors for the delivery of nucleic acids to cells include, for example, replication defective retrovirus, adenovirus, parvovirus (e.g., adeno-associated viruses), and coronavirus. Examples of retroviruses include avian leukosis-sarcoma, mammalian C-type, B-type viruses, lentiviruses (Coffin, J. M., "Retroviridae: The Viruses and Their Replication", In: Fundamental Virology, Third Edition, B. N. Fields, et al., eds., Lippincott-Raven Publishers, Philadelphia, Pa., (1996)). The mechanism of infectivity depends upon the viral vector and target cell. For example, adenoviral infectivity of HeLa cells occurs by binding to a viral surface receptor, followed by receptor-mediated endocytosis and extrachromasomal replication (Horwitz, M. S., "Adenoviruses" In: Fundamental Virology, Third Edition, B. N. Fields, et al., eds., Lippincott-Raven Publishers, Philadelphia, Pa., (1996)).

The present invention is illustrated by the following examples, which are not intended to be limiting in any way.

EXAMPLES

Experimental Procedures

The following experimental procedures were used in the examples which follow.

Targeted disruption of the EphrinB2 gene. A 200 base pair probe starting from the ATG of the mouse EphrinB2 gene (Bennett, B. D., et al., Proc. Natl. Acad. Sci. USA 92:1866-1870 (1995)) was used to screen a 129SVJ genomic library (Stratagene). Analysis of several overlapping clones revealed that the first exon, including the signal sequence, ends at 131 base pairs after the ATG. Further phage analysis and library screens revealed that the rest of the EphrinB2 gene was located at least 7 kb downstream from the first exon. To construct a targeting vector (FIG. 1B), a 3 kb XbaI-NcoI fragment whose 3' end terminated at the ATG was used as the 5' arm. A 5.3 kb Tau-lacZ coding sequence (Mombaerts, P., et al., Cell 87:675-686 (1996)) was fused in frame after the ATG. The PGKneo gene (Ma, Q., et al., Neuron 20:469-482 (1998)) was used to replace a 2.8 kb intronic sequence 3' to the first exon. Finally, a 3.2 kb downstream EcoRI-EcoRI fragment was used as the 3' arm. Normal (6 kb) and targeted (9 kb) loci are distinguished by HindIII digestion when probed with a 1 kb HindIII-XbaI genomic fragment. Electroporation, selection and blastocyst-injection of AB-1 ES cells were performed essentially as described Ma, Q., et al. (Neuron 20:469-482 (1998)), with the exception that FIAU-selection was omitted. ES cell targeting efficiency via G418 selection was 1 out of 18 clones. Germline transmission of the targeted EphrinB2 locus (FIG. 1C) in heterzygous males was confirmed by Southern blotting of tail DNA of adult mice, using a 1 kb HindIII-XbaI probe. Subsequent genotyping was done by genomic PCR. Primers for Neo are 5'-AAGATGGATTGCACGCAGGTTCTC-3' (SEQ ID NO.: 1) and 5'-CCTGATGCTCTTCGTCCAGATCAT-3' (SEQ ID NO.: 2). Primers for the replaced intronic fragment are 5'-AGGACGGAGGACGTTGCCACTAAC-3' (SEQ ID NO.: 3) and

5'-ACCACCAGTTCCGACGCGAAGGGA-3' (SEQ ID NO.: 4).

LacZ, PECAM-1, and histological staining. Embryos and yolk sacs were removed between E7.5 and E10.0, fixed in cold 4% paraformaldehyde/PBS for 10 minutes, rinsed twice with PBS, and stained for 1 hour to overnight at 37° C. in X-gal buffer (1.3 mg/ml potassium ferrocyanide, 1 mg/ml potassium ferricyanide, 0.2% Triton X-100, 1 mM $MgCl_2$, and 1 mg/ml X-gal [5-bromo-4-chloro-3-indolyl-β-D-galactopyranoside] in PBS, pH 7.2). LacZ stained embryos were post-fixed and photographed, or sectioned on a cryostat after embedding in 15% sucrose and 7.5% gelatin in PBS. Procedures for whole mount or section staining with anti-PECAM-1 antibody (clone MEC 13.3, Pharmingen) were done essentially as described Ma et al (*Neuron* 20:469-482 (1998); Fong et al., *Nature* 376:66-70 (1995)). Horseradish peroxidase-conjugated secondary antibodies were used for all PECAM-1 stainings. LacZ-stained yolk sacs were sectioned in gelatin and then subjected to hematoxylin counter-staining by standard procedures.

In situ hybridization. In situ hybridization on frozen sections was performed as previously described (Birren et al. *Development* 119:597-610 (1993)). Whole-mount in situ hybridization followed a protocol by Wilkinson, D. G., (Whole-mount in situ hybridization of vertebrate embryos. pp. 75-83 In: In Situ Hybridization: A Practical Approach (ed. D. G. Wilkinson) IRL Press, Oxford: 75-83 (1992). Bluescript vectors (Stratagene) containing cDNAs for EphB2/Nuk and EphB4/Myk-1 were generated as described Wang, H. U. and Anderson, D. J. (*Neuron* 18:383-396 (1997)).

Example 1

Targeted Mutagenesis of EphrinB2 in Mice

Targeted disruption of the EphrinB2 gene was achieved by homologous recombination in embryonic stem cells. The targeting strategy involved deleting the signal sequence and fusing a tau-lacZ indicator gene in frame with the initiation codon. The expression pattern of β-galactosidase in heterozygous (EphrinB2$^{tlacZ/+}$) embryos was indistinguishable from that previously reported for the endogenous gene. (Bennett, B. D. et al. *Proc. Natl. Acad. Sci. USA* 92: 1866-1870 (1995); Bergemann, A. D. et al. *Mol. Cell. Bio.* 1995:4921-4929 (1995); Wang, H. U. and Anderson, D. J. *Neuron* 18:383-396 (1997)). While prominent expression was detected in the hindbrain and somites, lower levels were observed in the aorta and heart as early as E8.25. Expression in the yolk sac was first detected at E8.5. Heterozygous animals appeared phenotypically normal. In homozygous embryos, growth retardation was evident at E10 and lethality occurred with 100% penetrance around E11. No expression of endogenous EphrinB2 mRNA was detected by in situ hybridization, indicating that the mutation is a null. Somite polarity, hindbrain segmentation, and the metameric patterning of neural crest migration (in which EphrinB2 and related ligands have previously been implicated Xu, W. et al. *Development* 121:4005-4016 (1995); Wang, H. U. and Anderson, D. J. *Neuron* 18:383-396 (1997); Krull, C. E. et al. *Curr. Biol.* 7:571-580 (1997); Smith, A. et al. *Curr. Biol.* 7:561-570 (1997)) appeared grossly normal in homozygous mutant embryos.

Example 2

Reciprocal Expression Pattern of EphrinB2 and EphB4 in Arteries and Veins

The enlarged heart observed in dying mutant embryos prompted examination of the expression of EphrinB2$^{tlacZ}$ in the vascular system in detail. Expression was consistently observed in arteries but not veins. In the yolk sac, for example, the posterior vessels connected to the vitelline artery, but not the vitelline vein, expressed the gene, as detected by lacZ staining. In the trunk, labeling was detected in the dorsal aorta, vitelline artery, umbilical artery and its allantoic vascular plexus, but not the umbilical, anterior and common cardinal veins (the umbilical vein is labeled with anti-PECAM-1 antibody). In the head, labeling was seen in branches of the internal carotid artery, but not in those of the anterior cardinal vein. In situ hybridization with EphrinB2 cDNA probes confirmed that the selective expression of tau-lacZ in arteries correctly reflected the pattern of expression of the endogenous gene. Examination of the expression of the four EphB family genes, as well as EphA4/Sek1, which are receptors for EphrinB2 Gale, N. W. et al., *Neuron* 17:9-19 (1996) revealed complementary expression of EphB4 in veins but not arteries, including the vitelline vein and its branches in anterior portion of the yolk sac.

Example 3

Vasculogenesis occurs Normally in EphrinB2 Mutant Embryos

The formation of the major vessels in the trunk was unaffected by the lack of EphrinB2, as examined by lacZ and PECAM-1 double staining of 9 somite embryos. Expression of EphrinB2-lacZ was seen in the dorsal aorta and vitelline artery, but not the umbilical and posterior cardinal veins. The dorsal aorta, vitelline artery, posterior cardinal and umbilical veins, for example, formed, although some dilation and wrinkling of the vessel wall was observed. Similarly the intersomitic vessels originating from the dorsal aorta formed at this stage. Between E8.5 and E9.0, the primitive endocardium appeared only mildly perturbed in mutants, while a pronounced disorganization was apparent at E10. Red blood cells developed and circulated normally up to E9.5 in both the mutant yolk sac and embryo proper.

Example 4

Extensive Intercalation of Yolk Sac Arteries and Veins Revealed by EphrinB2 Expression In the yolk sac, the vitelline artery and its capillary network occupy the posterior region, and the vitelline vein and its capillaries the anterior region. At E8.5, a stage at which the primary capillary plexus has formed but remodeling has not yet occurred, asymmetric expression of EphrinB2-taulacZ in heterozygous embryos was evident at the interface between the anterior and posterior regions. Apparently homotypic remodeling of β-galactosidase arterial capillaries into larger, branched trunks clearly segregated from venous vessels was evident between E9.0 and E9.5. At this stage, expression of the receptor EphB4 was clearly visible on the vitelline veins but not arteries. Thus arterial and venous endothelial capillaries are already molecularly distinct following vasculogenesis and prior to angiogenesis.

While textbook diagrams (Carlson, B. M *Patten's Foundations of Embryology* (1981)) of the yolk sac capillary plexus depict a non-overlapping boundary between the arterial and venous capillary beds, expression of EphrinB2-taulacZ allowed detection of a previously-unrecognized extensive intercalation between arteries and veins across the entire anterior-posterior extent of the yolk sac; this was observed in the heterozygote, but not in the homozygote. Double-labeling for PECAM and β-galactosidase revealed that the interface between the arteries and veins occurs between microvessel extensions that bridge larger vessels interdigitating en passant.

Example 5

Disrupted Angiogenesis in the Yolk Sac of EphrinB2$^{tlacZ}$/EphrinB2$^{tlacZ}$ Embryos Defects in yolk sac angiogenesis was were apparent by E9.0 and obvious at E9.5. There was an apparent block to remodeling at the capillary plexus stage, for both arterial vessels as revealed by β-galactosidase staining and venous vessels in the anterior region of the sac as revealed by PECAM staining. Thus, disruption of the EphrinB2 ligand gene caused both a non-autonomous defect in EphB4 receptor-expressing venous cells, and an autonomous defect in the arteries themselves.

This defect was accompanied by a failure of intercalating bi-directional growth of arteries and veins across the antero-posterior extent of the yolk sac, so that an interface between EprhinB2-expressing and non-expressing zones at the midpoint of the sac was apparent. (However, small patches of lacZ expression were occasionally visible within the anterior venous plexus, suggesting that some arterial endothelial cells may have become incorporated into venous capillaries.) These observations imply a close relationship between the remodeling of the capillary plexus into larger vessels and the intercalating growth of these vessels. The large β-galactosidase$^+$ vitelline arteries as well as vitelline veins present at the point of entry to the yolk sac of the embryo-derived vasculature appeared unperturbed in the mutant, however. This is consistent with the observation that the mutation does not affect formation of the primary trunk vasculature. It also argues that the yolk sac phenotype is due to a disruption of intrinsic angiogenesis and is not secondary to a failure of ingrowth of embryo-derived vessels.

Histological staining (hematoxylin) of sectioned yolk sacs revealed an accumulation of elongated support cells (mesenchymal cells or pericytes) in close association with the endothelial vessels at E10 and E10.5. In mutant yolk sacs, these support cells appeared more rounded, suggesting a defect in their differentiation. Moreover, in contrast to heterozygous yolk sacs, where vessels of different diameters began to appear at E9.5 and vessel diameter increased through E10.5, capillary diameter appeared relatively uniform and did not increase with age in the mutants. At E10.5, arteries appear dilated, as if fusion of vessels occurred without encapsulation by support cells. The mutant capillaries also failed to delaminate from the basal endodermal layer.

Example 6

Absence of Internal Carotid Arterial Branches and Defective Angiogenesis of Venous Capillaries in the Head of Mutant Embryos Similar to the yolk sac phenotype, the capillary bed of the head appeared dilated in the mutant, and apparently arrested at the primary plexus stage. Staining for β-galactosidase revealed that the anterior-most branches of the internal carotid artery failed to develop in the mutant. Unlike the case in the yolk sac, therefore, the malformed capillary beds must be entirely of venous origin. However the anterior branches of the anterior cardinal vein formed although they were slightly dilated. Taken together, these data indicate that in the head, venous angiogenesis is blocked if the normal interaction with arterial capillaries is prevented. The angiogenic defects observed in the head and yolk sac are unlikely to be secondary consequences of heart defects (see below), since they are observed starting at E9.0 and the embryonic blood circulation appears normal until E9.5.

Example 7

EphrinB2-Dependent Signaling Between Endocardial Cells is Required for Myocardial Trabeculae Formation Examination of ligand and receptor expression in wild-type hearts revealed expression in the atrium of both EphrinB2 (as detected by lacZ staining) and EphB4 (as detected by in situ hybridization). Expression of both ligand and receptor was also detected in the ventricle in the endocardial cells lining the trabecular extensions of the myocardium. Double-labeling experiments suggested that the ligand and receptor are expressed by distinct but partially overlapping cell populations, although the resolution of the method does not permit us to distinguish whether this overlap reflects co-expression by the same cells, or a close association of different cells. In any case, expression of EphrinB2 and EphB4 does not define complementary arterial (ventricular) and venous (atrial) compartments of the heart, unlike the extra-cardiac vasculature.

Heart defects commenced at E9.5 and were apparent in mutant embryos at E10 both morphologically and by whole-mount PECAM-1 staining. Sections revealed an absence of myocardial trabecular extensions, although strands of EphrinB2-expressing endocardial cells were still visible. Thus, mutation of the ligand-encoding gene caused a non-autonomous defect in myocardial cells, similar to the effect of a mutation in the neuregulin-1 gene. (Meyer, D. and Birchmeier, C, *Nature* 378:386-390 (1995)) Paradoxically, however, in this case the EphB4 receptor is expressed not on myocardial cells, as is the case for the neuregulin-1 receptors erbB2 and erbB4 (Lee et al., *Nature* 378:394-398 (1995); Gassmann, et al., *Nature* 378:390-394 (1995), but rather on endocardial cells. Expression of any of the other receptors for Ephrin B family ligands (Eph B1, B2, B3 and A4) was detected in this tissue. This suggests that in the heart, ligand-receptor interactions among endothelial cells may in turn affect interactions with smooth muscle cells.

Example 8

Ephrin B2 is Required for Vascularization of the Neural Tube

In EphrinB2$^{tlacZ}$/EphrinB2$^{tlacZ}$ embryos capillary ingrowth into the neural tube failed to occur. Instead, EphrinB2-expressing endothelial cells remained associated with the exterior surface of the developing spinal cord. Comparison of β-galactosidase to pan-endothelial PECAM-1 and EphB4 expression provided no evidence of a separate, venous capillary network expressing EphB4 in the CNS at this early stage (E9-E10). Rather, expression of a different EphrinB2 receptor, Eph B2, was seen in the neural tube as previously reported Henkemeyer, et al., *Oncogene* 9:1001-1014 (1994), where no gross morphological or patterning defects were detectable. In this case, therefore, the mutation does not appear to cause a non-autonomous phenotype in receptor-expressing cells, rather only an autonomous effect on ligand-expressing cells.

Example 9

EphrinB2 is Artery-Specific in Adult Tissues

To determine whether ephrin-B2 is expressed in adult tissues in an artery-specific manner, we performed histochemical staining for β-galactosidase on ephrin-B2$^{taulacZ}$/+ heterozygous mice. Antibody staining for PECAM-1, a pan-endothelial marker, was performed on the same or on adjacent sections to reveal non-arterial vessel (i.e., veins). Ephrin-B2 is expressed throughout the adult mouse in an artery-specific manner, in tissues including the heart, leg muscle, kidney, liver and fat. Expression was detected in vessels of all diameters, including large arteries, arterioles and the smallest-diameter capillaries. It had been previously assumed that capillaries by definition have neither arterial nor venous identity. These results show that this is not the case, and that arterial identity extends into the capillary beds.

Sections through adult arteries were double labeled by histochemical staining for β-galactosidase (lacZ) to reveal ephrin-B2-taulacZ expression, and with antibody to PECAM-1 as a pan-endothelial marker. LacZ (blue from X-gal) staining revealed ephrinB2 expression in dorsal aorta but not in inferior vena cava, in femoral artery next to the leg bone, but not in femoral vein, and in coronary epicardial artery, but not in coronary vein.

Similar staining of other sections revealed the presence of EphrinB2 in kidney arteriole, liver arteriole and small muscle arteriole, as well as arterial capillary. Kidney venule, hepatic vein, and muscle veins were lacZ-negative but PECAM-1 positive.

Gut fat was stained for lacZ (β-galactosidase) and labeled with PECAM-1 to reveal venous vessels as well as arterial vessels. EphrinB2 is expressed by arterioles and arterial capillaries and in arteriole but not in PECAM-1 positive venule. A further section showed that EphrinB2 is expressed by arterial capillaries surrounded by PECAM-1 positive non-arterial capillaries.

Example 10

Ephrin-B2 is Expressed during Tumor Angiogenesis

It had been assumed that tumor vessels sprout from the post-capillary venules. To address the question of whether EphrinB2 is expressed during tumor angiogenesis, Lewis Lung Carcinomas were implanted subcutaneously in the dorsal region of ephrin-B2$^{taulacZ}$/+ heterozygous females. After one week, the tumors were removed and processed for β-galactosidase histochemistry in whole mounts. The results indicate clearly that ephrin-B2 is in fact expressed by tumor vessels. This was confirmed by double-staining of sections cut through such tumors, for β-galactosidase and PECAM-1.

EphrinB2 expression by tumor capillaries. Lewis Lung Carcinoma (LLC) cells were implanted subcutaneously in the dorsal region of EphrinB2-taulacZ heterozygous females. After one week, tumors were removed for staining. EphrinB2 positive arterial capillaries were observed in peripheral tumor tissue. Double labeling with PECAM-1 colocalized the EphrinB2 lacZ (staining blue) and PECAM-1 (staining brown) signals in arterial capillaries, and reveals non-arterial capillaries labeled by PECAM-1 only.

Example 11

Screen for Clones Containing Artery-Specific Genes

A summary of the screening procedures used is provided in Appendix I. Briefly, endothelial cells were isolated from dissociated embryonic yolk sac, vitelline arteries or vitelline veins using positive selection with antibody to PECAM-1 (magnetic bead or FACS). cDNA was synthesized from lysates of either single cells or small numbers (ca. 200) of cells, and amplified by PCR. To confirm that the cDNAs were from arterial or venous endothelial cells, the cDNA synthesized from each cell prep was Southern blotted and hybridized in quadruplicate with a series of probes, including tubulin (ubiquitously expressed) the pan-endothelial probes Flk1 and Flt1, and the arterial-specific probe ephrin-B2. cDNAs that contained Flk1, Flt1 and ephrin-B2 sequences were considered arterial, while those that contained the pan-endothelial markers but not ephrin-B2 were considered venous. Thus the use of ephrin-B2 probes in this procedure was essential to confirm the arterial vs. venous nature of the cDNAs synthesized.

To isolate additional arterial-specific genes from these cDNAs, they were cloned into a phage lambda vector to generate cDNA libraries. Plaques from these libraries were then screened in duplicate filter lifts with arterial- or venous-specific cDNA probes made from either single cells or pools of cells. Plaques exhibiting differential hybridization to the arterial vs. venous probes were isolated, and the inserts were amplified using T3-T7 primers, and re-analyzed by cDNA Southern blotting. Two different pairs of arterial-venous endothelial cell cDNA probes (vitelline artery-vein cells and single yolk sac arterial and venous endothelial cells) were used in the Southern blot. Most of the clones were strongly expressed in arterial cells, and expressed weakly or not detectably by venous cells. The initial screen was designed to isolate additional arterial-specific genes. Twelve candidate arterial-specific clones were isolated using the single-cell probes, while one clone was isolated using the pooled probe.

The arterial-specific expression of these genes in vivo can be confirmed by in situ hybridization experiments. Methods such as these can be applied to arterial endothelial cells or vein-specific cells.

These data show that it will be possible to isolate novel arterial- or venous-specific genes from single endothelial cells. Such vessel type-restricted genes may provide insights into the physiological differences between arterial and venous endothelial cells. Methods such as those described herein can also identify genes involved in the etiology of arterial and venous specific diseases, such as arterial hypertension, atherosclerosis, deep venous thrombosis, and certain types of venous malformations. They can also provide candidate genes for human genetic disorders of the circulatory system. The gene products of such genes can then serve as novel drug targets.

APPENDIX I

Single Cell PCR, 3' cDNA Library Construction And Differential Screening Procedure to Isolate Novel Arterial- or Venous-Specific Genes 1. Dissection of vitelline arteries and vitelline veins from E12.5 to E14.5 yolk sacs, based on morphological criteria.
2. Dissociation of yolk sacs in collagenase solution (5 mg/ml) at 37° C. for 45'.
3. Isolate single or small groups of endothelial cells (ECs) by one of the following methods.
    a) Magnetic bead-based separation using PECAM-1 as primary antibody.
    b) FACS purification using PECAM-1-FITC primary antibody.
    c) GFP fluorescence from tie2-GFP transgenic mouse for endothelial cell identification, followed by microcapillary mouth-pipeting.
4. Lyse the single cells in PCR tubes at 65° C. for 1'.
5. Keep 1-2' at room temperature to allow the oligo-T to anneal to RNA.
6. Reverse transcription using AMV and MMLV enzyme mixture, at 37° C. for 15'.
7. Poly-A tailing with terminal transferase and dATP, at 37° C. for 15'.
8. PCR reaction set up:
    100 µl reaction, 5-fold normal level of dNTP mix, high concentration of Taq.
    Using a single PCR primer with 24 (T)s at 3' end for symmetrical amplification.
9. cDNA Southern blotting with endothelial specific and arterial/venous specific 3' probes on the amplified cDNAs for each cell prep.
10. Choose a few good cells that give strong signals for the appropriate probes. Isolate cDNAs from 500 bp to 2 kb on agarose gel.
11. Precipitate and quantify cDNA.
12. Ligate into lambda ZAPII (Stratagene; LaJolla, Calif.) phage arms for cDNA libraries.
13. Plate the library at very low density: 1000 pfu/plate. Take duplicate filter lifts.
14. Screen duplicate filters with probes made from vitelline artery cells and vitelline vein cells.
15. Pick differentially expressed phage clones. Reverse (cDNA) Southern blot confirmation of phage inserts by probing with probes made from vitelline artery cells and vitelline vein cells.
16. In situ hybridization to examine the expression patterns of cDNA fragments.

Example 12

Generation of Monoclonal Antibodies against the Extracellular Domain of Ephrin-B2

While polyclonal rabbit antibodies to fragments of ephrin-B2 expressed in bacteria had previously been reported, such antibodies are typically not reactive with native forms of the protein on the cell surface, and therefore are not useful for many applications including cell sorting, functional inhibition and drug-targeting. To generate antibodies with more desirable binding properties, we expressed the extracellular domain of ephrin-B2 as a glycophosphatidylinositol (GPI)-linked form on Chinese Hamster Ovary (CHO) cells. Hamsters were immunized with these cells, hybridomas prepared by fusion with mouse myeloma cells, and supernatants screened on COS cells expressing ephrin-B2-GPI.

Supernatant from clone #6E3 bound well to ephrinB2 on live COS cells. The ephrin-B2-GPI COS cell lines are a pooled population of G418-selected cells, with 30% of the cells being positive for ephrinB2. Control (untransfected) COS cells were negative when stained with the same antibody.

Example 13

Some Anti-Ephrin-B2 Antibodies Block the EphB2-EphrinB2 Binding Interaction

Figure 2:
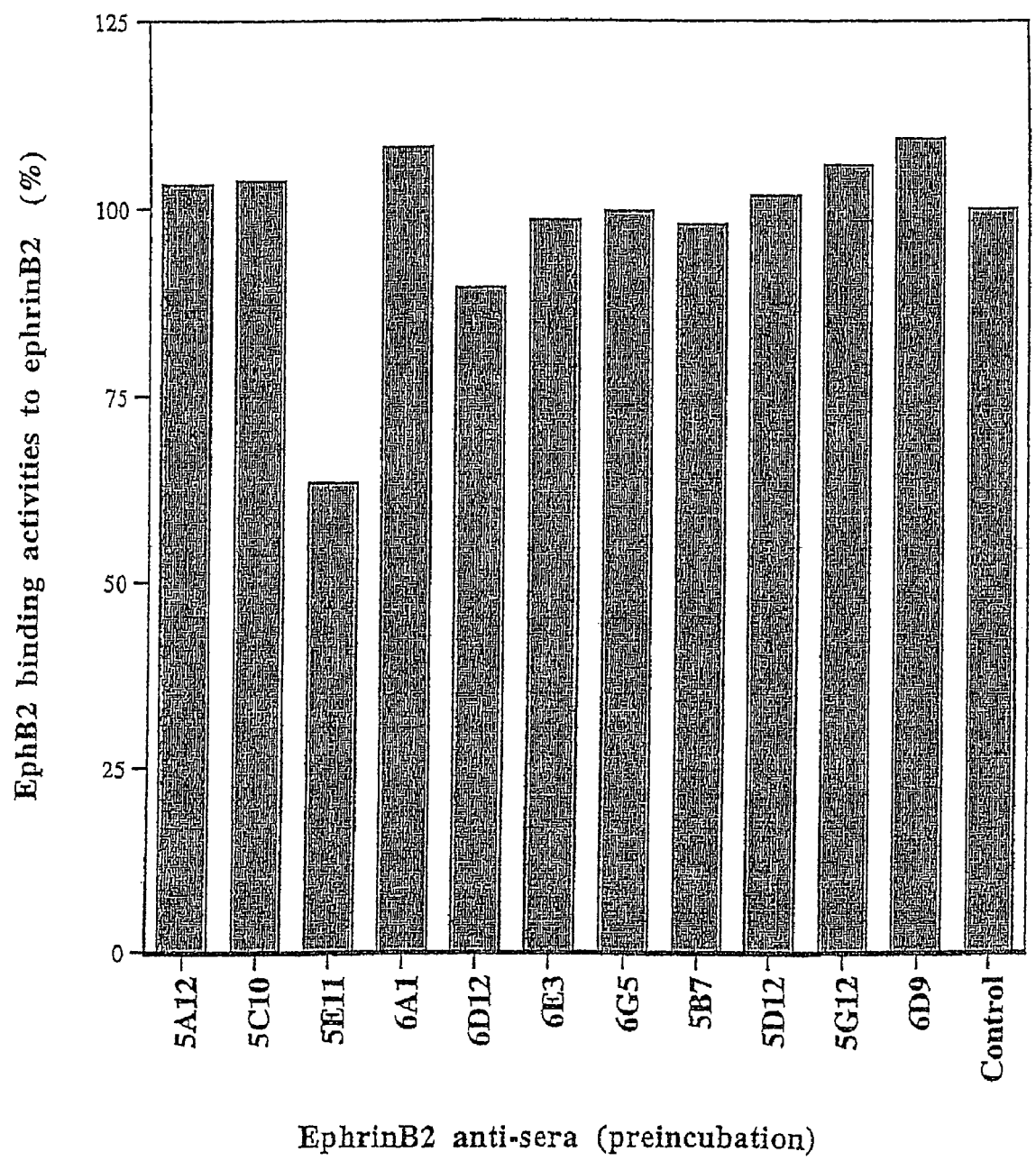
FIG. 2 is a bar graph indicating the binding activity to GPI-ephrin-B2 of EphB2Fc in the presence of hamster anti-ephrin-B2 hybridoma supernatants.

In cases where the antibodies also block function (i.e., inhibit binding of ephrin-B2 to its receptors), they can be used as potential anti-angiogenic agents. To demonstrate an assay to identify such function-inhibiting antibodies, we screened 12 hamster anti-EphrinB2 hybridoma supernatants for their ability to reduce the binding of GPI-ephrin-B2 (expressed on COS cells) to a soluble EphB2-Fc fusion protein. Binding was detected by $^{125}$I-labeled goat anti-human Fc antibody. Pre-incubation of cells with various supernatants revealed that the majority of the antibodies have no blocking effects on subsequent receptor-ligand binding (control as 100%), even though these supernatants all contained antibodies that bound to ephrin-B2-GPI. One of the antibodies produced a 40% reduction in EphB2-Fc binding to the ephrin-B2-GPI COS cells (FIG. 2).

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method for inhibiting angiogenesis in a mammal, comprising administering a therapeutically effective quantity of an antibody selected from the group consisting of: i) an antibody which specifically binds to EphriniB2; and ii) an antibody which binds to EphB4, wherein said antibody inhibits angiogenesis in an indicator mouse which comprises a reporter construct in a locus selected from the group consisting of the EphB4 locus and the EphB2 locus.

2. The method of claim 1, wherein the antibody is a polyclonal antibody.

3. The method of claim 1, wherein the antibody is a monoclonal antibody.

4. The method of claim 1, wherein the antibody is administered locally to a site of angiogenesis.

5. The method of claim 4, wherein the site of angiogenesis is a tumor.

6. The method of claim 4, wherein the mammal is a human.

7. The method of claim 1, wherein the antibody specifically binds to an extracellular domain of EphrinB2.

8. The method of claim 1, wherein the antibody specifically binds to EphB4.

* * * * *

UNITED STATES PATENT AND TRADEMARK OFFICE
CERTIFICATE OF CORRECTION

| | | |
|---|---|---|
| PATENT NO. | : 7,595,044 B2 | |
| APPLICATION NO. | : 11/028803 | |
| DATED | : September 29, 2009 | |
| INVENTOR(S) | : Wang et al. | |

It is certified that error appears in the above-identified patent and that said Letters Patent is hereby corrected as shown below:

In Claim 1, column 25, line 51, replace "EphriniB2" with

--EphrinB2--

Signed and Sealed this
Twenty-eighth Day of August, 2012

David J. Kappos
*Director of the United States Patent and Trademark Office*

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
aagatggatt gcacgcaggt tctc    24

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
cctgatgctc ttcgtccaga tcat    24

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
aggacggagg acgttgccac taac    24

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
accaccagtt ccgacgcgaa ggga    24